United States Patent [19]

Noda et al.

[11] 4,335,251
[45] Jun. 15, 1982

[54] PHENYL-I-PROPIONIC ACID ESTERS AND PHARMACEUTICAL USE THEREOF

[75] Inventors: Kanji Noda, Chikushino; Akira Nakagawa; Yuji Ishikura, both of Tosu; Hiroyuki Ide, Fukuoka, all of Japan

[73] Assignee: Hisamitsu Pharmaceutical Co. Inc., Saga, Japan

[21] Appl. No.: 175,498

[22] Filed: Aug. 5, 1980

Related U.S. Application Data

[63] Continuation of Ser. No. 956,446, Nov. 1, 1978, abandoned, which is a continuation of Ser. No. 748,454, Dec. 8, 1976, abandoned.

[51] Int. Cl.³ .................................. C07B 69/76
[52] U.S. Cl. ............................. 560/105; 424/308; 260/465 R; 260/544 D; 562/496; 260/546
[58] Field of Search ..................... 560/105; 424/308

[56] References Cited

U.S. PATENT DOCUMENTS

| | | | |
|---|---|---|---|
| 3,228,831 | 1/1966 | Nicholson et al. | 560/105 |
| 3,452,079 | 6/1969 | Shen et al. | 560/105 |
| 3,586,709 | 6/1971 | Richter et al. | 560/61 |
| 3,965,161 | 6/1976 | Kogure et al. | 562/418 |
| 4,016,179 | 4/1977 | Fujimoto et al. | 260/347.5 |
| 4,150,137 | 4/1979 | Noda et al. | 424/263 |

FOREIGN PATENT DOCUMENTS 50-154217 12/1975 Japan .
1012480 12/1965 United Kingdom .

OTHER PUBLICATIONS

Niewiademski et al., Rocz. Chem., 1976 50(11) 1987-1989, Chem. Abs., vol. 86: 139565g, 1977.
Fontanella et al., as cited in CA, 70, 57451x, (1969).

*Primary Examiner*—Paul J. Killos
*Attorney, Agent, or Firm*—Browdy and Neimark

[57] ABSTRACT

The present invention relates to the phenyl-propionic acid ester derivative of the following formula:

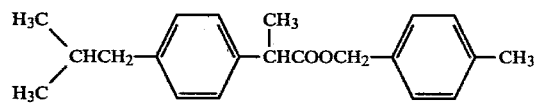

The compound obtained by the present invention possesses a high degree of analgetic, antipyretic and anti-inflammatory activity and causes little side effects on the gastro-intestinal tracts, when administered orally and topically, and it may be useful as an oral and topical analgesic, antipyretic and anti-inflammatory agent.

6 Claims, No Drawings

PHENYL-I-PROPIONIC ACID ESTERS AND PHARMACEUTICAL USE THEREOF

This is a continuation of application Ser. No. 956,446 filed Nov. 1, 1978, which in turn is a continuation application of Ser. No. 748,454, filed Dec. 8, 1976 both now abandoned.

DETAILED DESCRIPTION

The present invention relates to novel phenylpropionic acid ester derivative of the general formula [A]:

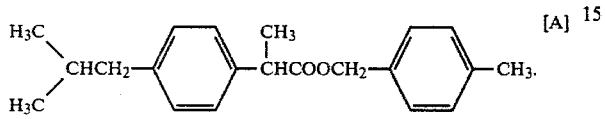

The compound of the present invention produces a high degree of analgetic, anti-pyretic and anti-inflammatory activity and little side effects on the gastro-intestinal tracts, when it is administered orally and topically. Therefore, it may be useful as oral and topical analgesic, antipyretic and anti-inflammatory agent.

Adrenalcortical hormone preparations have been used as predominant anti-inflammatory agents for external use. However, even when these preparations are applied topically, their long-term application may often cause outward side effects. Thus, non-steroidal anti-inflammatory agents with low toxicity have been demanded for a long time. For this reason, it is said that development of the compound of the present invention meets fully these demands.

The process for preparing the compound of the present invention may be explained in the following. The compound of the present invention may be obtained in high yields by any one of the following processes [I] to [VIII].

Process [I]:

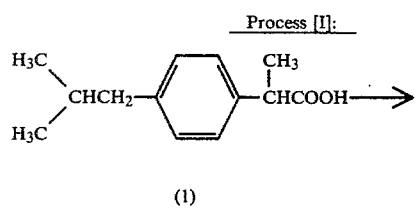

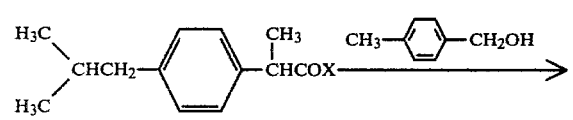

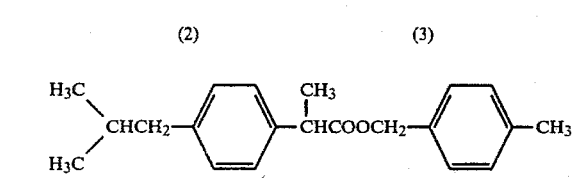

wherein X may be halogen.

Process [II]:

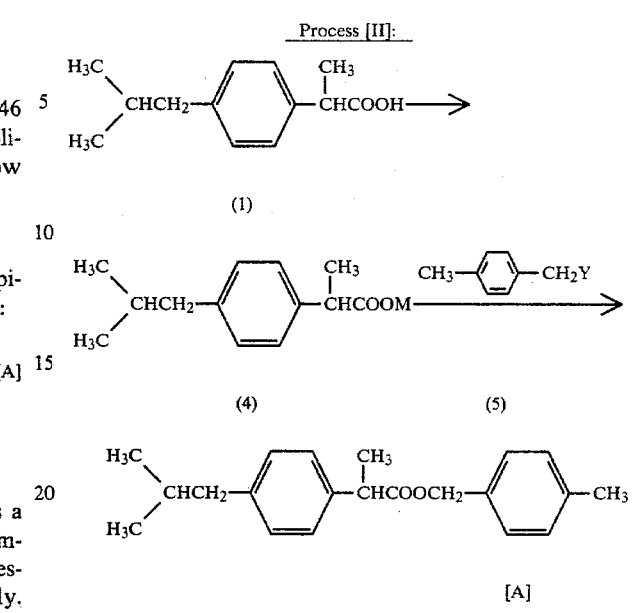

wherein, R has the same meanings as defined above; M may be alkali metal and Y is selected from halogen and organic sulfonyloxy.

Process [III]:

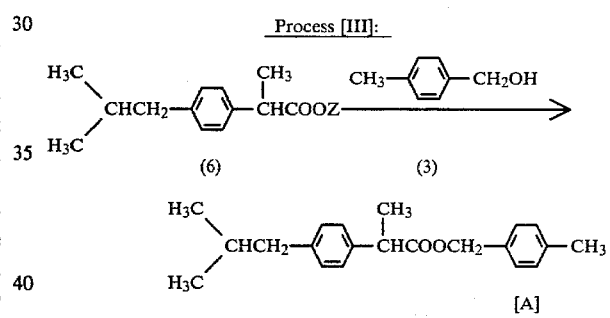

wherein Z may be lower alkyl.

Process [IV]:

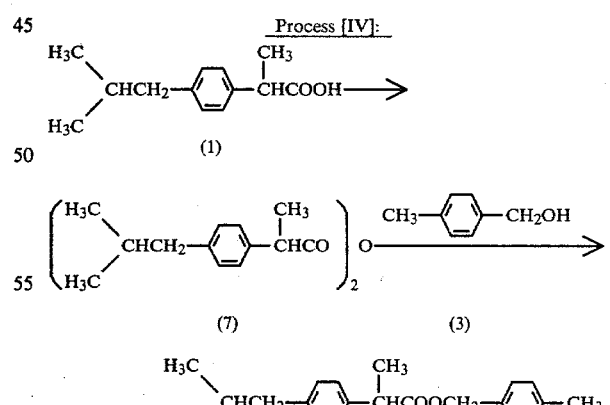

Process [V]:

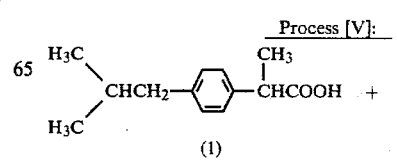

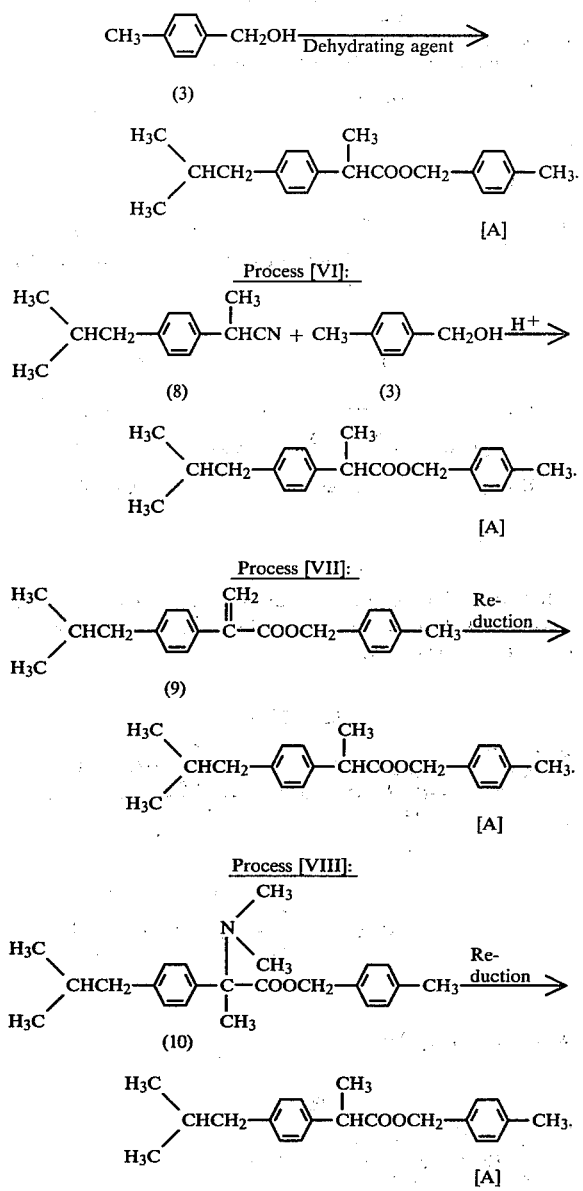

Further details of the processes shown by the aforesaid reaction schemes are given in the following.

In the process [I], the p-isobutylphenylpropionic acid of the formula (1) is treated with a halogenizing agent to produce its acid halide of the general formula (2). Subsequently, the acid halide is allowed to react with the alcohol of the formula (3) in an unreactive organic solvent such as tetrahydrofuran, diglyme, dioxane, acetone, chloroform, benzene or toluene in the presence of a dehydrating agent such as pyridine, trimethylamine, triethylamine, potassium carbonate or sodium carbonate.

In the process [II], the compound of the formula (1) is treated with alkali metal to produce the compound of the general formula (4), which is then allowed to react with the alkali halide of the general formula (5) in an organic solvent such as benzene, toluene, xylene, tetrahydrofuran, diglyme, dioxane, dimethylformamide or dimethylsulfoxide. The reaction proceeds smoothly even at room temperature, but promoted by application of heating.

In the process [III], to the compound of the general formula (6) is added the alcohol of the formula (3) in large excess to serve also as a reaction solvent. The resulting mixture is heated at or in the vicinity of the boiling point of the alcohol used either with or without adding a small amount of alkali metal to bring about ester interchange. For this reaction, benzene, toluene and xylene may also be used as other preferable solvents.

In the process [IV], the compound of the formula (7) is allowed to heat with the alcohol of the formula (3) in excess either with or without adding an acid catalyst. Other organic solvents which do not participate in the reaction may also be used for this reaction.

In the process [V], the compound of the formula (1) is reacted with the alcohol of the formula (3) under reflux in the presence of a dehydrating agent such as sulfuric acid poly-phosphoric acid or p-toluenesulfonic acid. Such organic solvents as benzene, toluene and xylene are used as preferable reaction solvents. The use of large excess of the alcohol (3) may also serve for reaction solvents.

In the process [VI], a nitrile of the formula (8) is heated with the alcohol of the formula (3) in the presence of an acid catalyst, for example, sulfuric acid to produce the ester derivative.

In the process [VII] and [VIII], the respective compounds of the formula (9) and (10) are allowed to reduce in the presence of a catalyst such as palladium carbon or platinum dioxide.

Compound

The compound of the present invention may be prepared by the aforesaid processes [I]–[VIII], and it is shown in Table I, including its appearance, boiling point and mass spectra(parent ion).

TABLE I $H_3C\text{\textbackslash}CHCH_2\text{-}C_6H_4\text{-}CHCOOCH_2\text{-}C_6H_4\text{-}CH_3$ / $H_3C$ / $CH_3$

| | |
|---|---|
| Appearance | Oil |
| Boiling point | 139–140/0.1mmHg |
| Mass spectrum (parent ion) | 310 |

The compound of the present invention was first tested for its acute toxicities, and subsequently for its pharmacological activities such as anti-inflammatory and analgesic activity. It is found that the compound of the present invention has shown a high degree of pharmacological activities with low toxicity. Especially, topical application of the said compound has produced a higher anti-inflammatory potency than that of ibuprofen. The testing methods are described in the following, and the results are summarized in Table II.

(1) Acute toxicity

Each test compound suspended in 0.5% tragacanth-saline was administered intraperitoneally or orally to male mice of dd-strain (body weight 16–24 g). The lethal dose was estimated from the death of animals 72 hours administration.

(2) Anti-inflammatory activity for oral route

A group of five male rats of Wistar-strain (body weight 100–150 g) were orally given each test compound suspended in 0.5% tragacanth-saline. After 30 minutes 0.5–1.0% carrageenin suspended in the water for injection was injected subcutaneously to a hind paw. After 3 hours the carrageenin edema was measured by volume, and the percent inhibition was determined with respect to the results for the control animals. For comparison, the percent inhibition of each test compound of the present invention was divided by that of the reference compound, ibuprofen [2-(p-isobutylphenyl)propionic acid] to give the relative inhibition, which is included in Table II. The mean percent inhibition of ibuprofen was 37.4% at a dose of 50 mg/kg and 33.5% at 10 mg/kg.

(3) Anti-inflammatory activity for topical route

The dorsal skin of male rates of Wistar-strain (body weight: about 100 g) were depilated. Carrageenin suspension was injected intra-dermally at a dose of 250 γ/0.05 ml/site. The filter paper (size: 2.3 cm in diameter) was impregnated with 1% test compound dissolved in polyethylene glycol 300. Immediately after injection, the filter paper containing 125.2±18.0 mg of the polyethylene glycol was applied on the injected site. After 3 hours, 1% pontamine sky blue solution was injected intravenously at a dose of 0.5 ml/kg. After further 3 hours, the animals were sacrificed and their dorsal skin were removed to measure the area of leakage of the pigment. The percent inhibition was determined with respect to the results for the control animals. For comparison, the percent inhibition of each test compound of the present invention was divided by that of the reference compound, ibuprofen, to give the relative inhibition. The mean percent inhibition of ibuprofen was 23.8%.

(4) Analgetic activity

Each test compound suspended in 0.5% tragacanth-saline was orally administered to dd-strain mice (body weight: 18–20 g). After one hour 0.6% acetic acid solution was injected intraperitoneally in a volume of 0.1 ml/10 g. The writhing syndrome was observed for 10 minutes from 30 minutes after injection, and 50% analgetic effective dose ($ED_{50}$) and its 95% confidence limit were calculated by Litchfield-Wilcoxon's method.

TABLE II

| | | | Ibuprofen | Object Compound of Formula [A] |
|---|---|---|---|---|
| anti-inflammatory effect | oral | 50 mg/kg | 1.0 | 1.5 |
| | | 10 mg/kg | 1.0 | 1.7 |
| | topical | | 1.0 | 1.9 |
| analgesic effect $ED_{50}$ (mg/kg) (95% C.L.) | | | 45.8 (42.1–49.5) | 229.6 (190.1–269.2) |

Pharmacological Effects and Acute Toxicity of the Object Compound obtained by the Present Invention:

EXAMPLE 1

To a solution of 5.4 g of 2-(4-isobutylphenyl)propionic acid chloride and 3.5 g of p-methylbenzyl alcohol in 30 ml of tetrahydrofuran was added 3.7 g of trimethylamine, dropwise under cooling, and reacted at room temperature for 2 hours. After the reaction was complete, the crystals produced were removed by filtration. The filtrate was freed of solvent by distillation to leave a residue, to which was added water. The resulting mixture was extracted with ether, and the extract was dehydrated and freed of solvent by distillation to give an oily residue. This residue was then distilled in vacuo to yield 6.3 g of 2-(4-isobutylphenyl)propionic acid-p-methylbenzyl ester as a colorless oil, boiling at 139°–140° C./0.1 mmHg. Mass spectrum: parent ion 310 m/e.

What is claimed is:

1. A composition of the following formula:

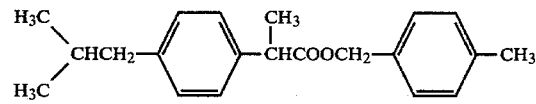

2. A method of treating inflammation comprising administering topically an anti-inflammatory amount of a compound in accordance with claim 1.

3. A method of treating a patient in need of an analgetic, antipyretic, or anti-inflammatory agent comprising orally administering an analgetic, antipyretic or anti-inflammatory amount of a compound in accordance with claim 1.

4. A method of alleviating symptoms of inflammation comprising orally or topically administering to a patient suffering such symptoms an anti-inflammatory amount of a compound in accordance with claim 1.

5. A method of alleviating the symptoms of pain which comprises orally administering to a patient suffering such symptoms an analgetic amount of a compound in accordance with claim 1.

6. A method of alleviating the symptoms of fever which comprises orally administering to a patient suffering such symptoms an antipyretic amount of a compound in accordance with claim 1.

* * * * *